United States Patent [19]

Melloni et al.

[11] Patent Number: 5,068,433

[45] Date of Patent: Nov. 26, 1991

[54] PROCESS FOR PREPARATION OF 3-SUBSTITUTED DERIVATIVES OF 1-AMINO-2-HYDROXY PROPANE

[75] Inventors: Piero Melloni, Bresso; Arturo D. Torre, Gallarate; Ettore Lazzari; Giuseppe Mazzini, both of Milan, all of Italy

[73] Assignee: Farmitalia Carlo Erba, S.r.l., Milan, Italy

[21] Appl. No.: 536,039

[22] Filed: Jun. 11, 1990

Related U.S. Application Data

[63] Continuation of Ser. No. 349,965, May 8, 1989, abandoned, which is a continuation of Ser. No. 227,414, Jul. 29, 1988, abandoned, which is a continuation of Ser. No. 16,505, Jan. 27, 1987, abandoned, which is a continuation of Ser. No. 751,858, Jul. 5, 1985, abandoned.

[30] Foreign Application Priority Data

Aug. 2, 1984 [GB] United Kingdom ................. 8419683

[51] Int. Cl.$^5$ .................. C07G 217/44; C07G 217/64
[52] U.S. Cl. ..................................... 564/349; 564/348
[58] Field of Search .................... 564/304, 348, 349

[56] References Cited

U.S. PATENT DOCUMENTS

| | | | |
|---|---|---|---|
| 2,252,039 | 8/1941 | Schirm | 549/553 X |
| 2,977,374 | 3/1961 | Phillips et al. | 549/555 X |
| 3,538,150 | 11/1970 | Gilman et al. | 564/349 X |
| 3,780,081 | 12/1973 | LeCourt et al. | 564/345 X |
| 3,987,086 | 10/1976 | Dexter et al. | 549/555 X |
| 4,085,136 | 4/1978 | Tucker | 564/349 |
| 4,120,974 | 10/1978 | Frater et al. | 549/563 X |
| 4,229,449 | 10/1980 | Melloni et al. | 564/348 |
| 4,263,325 | 4/1981 | Carlsson et al. | 564/349 X |
| 4,271,160 | 6/1981 | Melloni et al. | 564/348 X |
| 4,341,718 | 7/1982 | Kim et al. | 564/347 |
| 4,777,291 | 10/1988 | Misner | 564/304 |

*Primary Examiner*—Glennon H. Hollrah
*Assistant Examiner*—Brian Bembenick
*Attorney, Agent, or Firm*—Armstrong, Nikaido, Marmelstein, Kubovcik & Murray

[57] ABSTRACT

The present invention relates to a new process for the preparation of 3-substituted derivatives of 1-amino-2-hydroxy-propane in the form of single diastereoisomers, to certain of these diastereoisomers, and to compounds which are intermediates in the new process of the invention.

1 Claim, No Drawings

PROCESS FOR PREPARATION OF 3-SUBSTITUTED DERIVATIVES OF 1-AMINO-2-HYDROXY PROPANE

This application is a continuation of application Ser. No. 349,965 filed May 8, 1989, now abandoned, which is a continuation of application Ser. No. 227,414 filed July 29, 1988, now abandoned, which is a continuation of application Ser. No. 016,505 filed Jan. 27, 1987, now abandoned, which is a continuation of Ser. No. 751,858, filed July 5, 1985, now abandoned.

The present invention relates to a new process for the preparation of 3-substituted derivatives of 1-amino-2-hydroxy-propane in the form of single diastereoisomers, to certain of these diastereoisomers, and to compounds which are intermediates in the new process of the invention.

According to the invention, single diastereoisomers of 3-substituted derivatives of 1-amino-2-hydroxy-propane of the following formula (I)

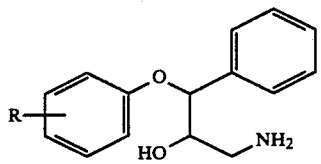

(I)

wherein R is $C_1$–$C_6$ alkoxy or tri-halomethyl, are prepared by a process comprising:

(a) epoxidizing trans-cinnamic alcohol, so obtaining the compound of formula (II)

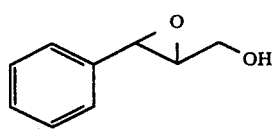

(II)

(b) reacting the compound of formula (II) with a phenol derivative of formula (III)

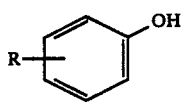

(III)

wherein R is as defined above, so obtaining a 3-substituted-1,2-dihydroxy propane derivative of formula (IV)

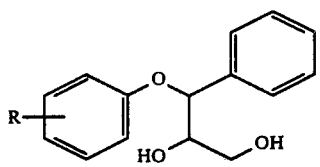

(IV)

wherein R is as defined above; and either (c) esterifying a compound of formula (IV) with a sulfonic acid, or a reactive derivative thereof, so obtaining a monoester of formula (V)

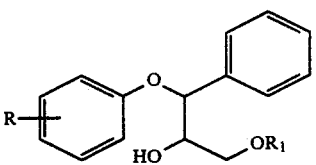

(V)

wherein R is as defined above and $R_1$ is the residue of a sulfonic acid, and then reacting a compound of formula (V) with ammonia so obtaining one diastereoisomer of formula (I); or, in alternative, (d) esterifying a compound of formula (IV) with a carboxylic acid, or a reactive derivative thereof, so obtaining a compound of formula (VI)

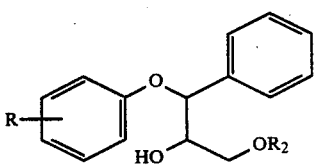

(VI)

wherein $R_2$ is the residue of a carboxylic acid and R is as defined above;

(e) esterifying a compound of formula (VI) with a sulfonic acid, or a reactive derivative thereof, so obtaining a diester of formula (VII)

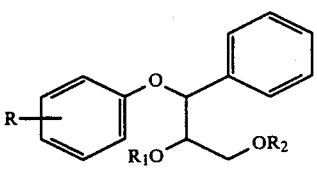

(VII)

wherein R, $R_1$ and $R_2$ are as defined above;

(f) making an epoxide from a compound of formula (VII), so obtaining a compound of formula (VIII)

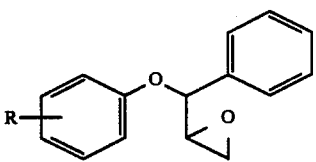

(VIII)

wherein R is as defined above, and then reacting a compound of formula (VIII) with ammonia, so obtaining the other diastereoisomer of formula (I).

In the above formulae, when R is $C_1$–$C_6$ alkoxy preferred groups are methoxy and ethoxy, in particular ethoxy. When R is tri-halo-methyl, trifluoromethyl is preferred. Preferably R is an ethoxy group in the ortho-position of the benzene ring.

A sulfonic acid is, for example, methanesulfonic acid or p-toluenesulfonic acid.

A carboxylic acid may be either aliphatic or aromatic. An aliphatic carboxylic acid may be, for example, a $C_2$–$C_6$ carboxylic acid such as, for instance, acetic acid or propionic acid.

An aromatic carboxylic acid is, for instance, an optionally substituted benzoic acid, such as, e.g., benzoic acid and p-nitro-benzoic acid.

A reactive derivative of a either sulfonic or carboxylic acid may be, for example, a corresponding halide, e.g. the chloride, or the corresponding anhydride or a mixed anhydride.

Thus, for example, the $R_1$ residue of a sulfonic acid, in the above formulae (V) and (VII) is, e.g., methanesulfonyl or p-toluenesulfonyl; preferably $R_1$ is p-toluenesulfonyl in formula (V) and methanesulfonyl in formula (VII).

Similarly the $R_2$ residue of a carboxylic acid in the above formulae (VI) and (VII) is, e.g., acetyl, propionyl, benzoyl or p-nitro-benzoyl.

As already said, the new process of the invention allows to obtain compounds of formula (I) in the form of single diastereoisomers: these, in accordance with IUPAC, Nomenclature of Organic Chemistry Sections A, B, C, D, E, F and H, 1979 Edition, can be referred to as (RS,RS) and, respectively, (RS,SR) diastereoisomers, each diastereoisomer involving, as is known, a couple of enantiomers. Accordingly, a (RS,RS) diastereoisomer is intended to be a racemate of (R,R) and (S,S) enantiomers, and a (RS,SR) diastereoisomer is intended to be a racemate of (R,S) and (S,R) enantiomers.

When the new process of the invention is carried out through the steps (a), (b) and (c), a (RS,SR) diastereoisomer is obtained; when the process is carried out through the steps (a), (b), (d), (e) and (f), then a (RS,SR) diastereoisomer is obtained.

The epoxidation of the trans-cinnamic alcohol to give the epoxide of formula (II) may be carried out by the use of a suitable oxidizing agent, for instance with vanadic anhydride and hydrogen peroxide, or with a peroxy acid such as, e.g., perbenzoic, m-chloroperbenzoic, peracetic, mono- or di-peroxy-phthalic, or peroxy-trifluoroacetic acid.

The reaction may be carried out at any suitable temperature between room temperature and the boiling point of the used solvent, preferably at room temperature, in an appropriate solvent which may be, for example, an optionally halogenated hydrocarbon, e.g. benzene, chloroform or methylene chloride, or a linear or cyclic ether, e.g. dioxane, or also acetic acid.

The reaction between a compound of formula (II) and a compound of formula (III) is preferably carried out by heating at a temperature between about 60° C. and about 120° C., in the presence of a base such as, e.g., aqueous sodium or potassium hydroxide, preferably in the absence of any other solvent.

The esterification of a compound of formula (IV) to give a compound of formula (V) is preferably carried out with a reactive derivative of a sulfonic acid, preferably a sulfonic acid halide, in particular the chloride, e.g. methanesulfonyl chloride or p-toluenesulfonyl chloride, in the presence of an acid acceptor which may be, for instance, an organic base such as, e.g., triethylamine or pyridine.

The reaction is preferably performed under cooling, e.g., at $-10° \div 50°$ C., in particular at $-10° \div 0°$ C., in a suitable anhydrous solvent such as, e.g., benzene, toluene or pyridine: when pyridine is used as solvent, it also acts as a base.

The reaction of a compound of formula (V) with ammonia to give one, (RS,SR), diastereoisomer of formula (I) is preferably carried out at a temperature between about 0° C. and the room temperature, in particular at room temperature, with 30–32% aqueous ammonia in a suitable solvent which may be, for instance, dimethylacetamide or an aliphatic alcohol, e.g. methanol or ethanol.

The esterification of a compound of formula (IV) to give a compound of formula (VI) is preferably performed with a reactive derivative of a carboxylic acid, preferably a carboxylic acid halide, in particular chloride, operating under cooling, e.g. at $-10° \div 50°$ C., in particular at about $-10° \div 0°$ C. or at room temperature, in an anhydrous organic solvent, e.g. benzene or toluene, in the presence of a base which may be, for example, an organic base such as, e.g., triethylamine or pyridine: according to a preferred procedure, pyridine is used as solvent in absence of any other base.

The subsequent esterification of a compound of formula (VI) to give a compound of formula (VII) is carried out using reaction conditions similar to those described hereabove for the conversion of a compound of formula (IV) into a compound of formula (V).

The transformation of a compound of formula (VII) into a compound of formula (VIII), is carried out by reaction with a suitable base, preferably an inorganic base such as, e.g., an alkali metal or alkaline-earth metal hydroxide, preferably sodium or potassium hydroxide.

Preferably the reaction is carried out at a temperature between about 0° C. and about 50° C., in particular at room temperature in an aqueous organic solvent such as, e.g., dioxane or dimethylformamide.

The subsequent reaction of the epoxide of formula (VIII) with ammonia, to give the other, (RS,RS), diastereoisomer of formula (I), may be performed using conditions similar to those reported above for the analogous reaction on a compound of formula (V).

The compounds of formula (II) and the compounds of formula (III) are known, commercially available products. While diastereoisomeric mixtures of compounds of formula (I) are known (U.K. patent specification 2,014,981B), compounds of formula (I) in the form of single diastereoisomers are only partially known.

The invention provides, therefore, as a further object, compounds of the above formula (I) wherein R is ethoxy or trifluoromethyl, in the form of the single diastereoisomers.

Object of the invention are also single diastereoisomers of the compounds having the above reported formulae (IV), (V), (VI), (VII) and (VIII).

Following known methods, e.g. same step sequences as those described in U.K. patent specification 2,014,981B, single (RS,RS) or (RS,SR) diastereoisomers of formula (I) obtained by the new process of the invention may be converted into corresponding single (RS,RS) or, respectively, (RS,SR) morpholine diastereoisomers: the latter are described too in U.K. patent specification 2,014,981B and are therein reported as being very useful antidepressant agents.

The following examples illustrate but do not limit the invention.

EXAMPLE 1

To a solution of trans-cinnamic alcohol(20 g) in methylene chloride (550 ml), cooled to 0°–5° C., 77% aqueous m-chloro-perbenzoic acid (36 g) was added in a period of 75 minutes.

The reaction mixture was left to rise to room temperature and stirring was continued for 2.5 hours. The formed m-chloro-benzoic acid was filtered under vacuum and washed with fresh methylene chloride. The organic phase was washed with sodium metabisulfite aqueous solution, with 20% aqueous $Na_2CO_3$, and then with a saturated NaCl aqueous solution; finally it was dried over Na$_2$SO$_4$ and filtered and the solvent was removed under reduced pressure with external temperture of 35° C., to give trans-3-phenyl-2-hydroxymethyl-oxirane (20.7 g) as a clear oil, NMR (CDCl$_3$)

| 90 MHz δ: | 2.70 (1H, br) | |
|---|---|---|
| | 3.22 (1H, dt) | |
| | 3.95 (1H, d) | J = 2.1 Hz |
| | 3.76 (1H, dd) | |
| | 4.04 (1H, dd) | |
| | 7.32 (5H, bs) | |

EXAMPLE 2

To a solution of NaOH pellets (2.66 g) in water (10 ml) 2-ethoxy-phenol (27.6 g) was added dropwise under vigorous stirring and inert gas atmosphere, and with an external bath at 70° C.

The solid which formed during the addition dissolved in 15–30 minutes and then trans-3-phenyl-2-hydroxymethyl-oxirane (11.76 g) was added.

The reaction mixture was stirred 2.5 hours at 70° C. then poured into 1N aqueous NaOH (250 ml), keeping the temperature at 10°–15° C. with an external water water bath, and finally extracted with methylene chloride. The organic phase was washed with NaCl saturated aqueous solution, dried over Na$_2$SO$_4$, filtered and the solvent was removed under vacuum keeping the external temperature at 35° C. The oily residue was treated with n-hexane to give 1.72 g of 1,2-dihydroxy-3-(2-ethoxy-phenoxy)-3-phenyl-propane, m.p. 68°–70° C., as RS,SR diastereoisomer.

EXAMPLE 3

To a solution of (RS,SR)-1,2-dihydroxy-3-(2-ethoxy-phenoxy)-3-phenyl-propane (5 g) in anhydrous pyridine (50 ml), cooled to −10° C., a solution of p-nitro-benzoylchloride (3.22 g) in anhydrous pyridine (50 ml) was added dropwise in 1.5 hours. After 30 minutes stirring at −10° C., the reaction mixture was poured into 2M aqueous HCl (1 l) and ice (600 g), then extracted with ethylacetate. The organic phase was successively washed with water (400 ml), a 5% aqueous NaHCO$_3$ solution (400 ml) and a saturated aqueous NaCl solution, and finally dried over Na$_2$SO$_4$ and filtered. Evaporation of the solvent under vacuum led to an oil which, upon treatment with n-hexane, was converted to 1-(4-nitrobenzoyloxy)-2-hydroxy-3-(2-ethoxy-phenoxy)-3-phenyl-propane as a solid product (4.5 g), m.p. 90°–92° C. (RS,SR diastereoisomer).

EXAMPLE 4

To a solution of (RS,SR)-1-(4-nitro-benzoyloxy)-2-hydroxy-3-(2-ethoxy-phenoxy)-3-phenyl-propane (4 g) in methylene chloride (45 ml) and triethylamine (1.93 ml), cooled to −5° C., methanesulfonyl chloride (0.77 ml) was added dropwise. After 1 hour stirring at −5° C., the reaction mixture was diluted with methylene chloride and successively washed with 10% aqueous HCl (50 ml), water (50 ml), a 5% aqueous solution of NaHCO$_3$ (50 ml) and saturated aqueous NaCl (50 ml). The separated organic phase was then dried over Na$_2$SO$_4$ and filtered and the solvent was evaporated under vacuum to give an oily residue which, upon treatment with isopropyl ether (30 ml), led to 3.95 g of solid 1-(4-nitro-benzoyloxy)-2-methanesulfonyloxy-3-(2-ethoxy-phenoxy)-3-phenyl-propane, m.p. 89°–90° C. as RS,SR diastereoisomer.

EXAMPLE 5

To a solution of (RS,SR)-1-(4-nitro-benzoyloxy)-2-methanesulfonyloxy-3-(2-ethoxy-phenoxy)-3-phenyl-propane (3.95 g) in dioxane (40 ml) 2N aqueous NaOH (16 ml) was added. After 4 hours stirring at room temperature the reaction mixture was poured in iced water (200 ml) and then extracted with ethyl acetate (200 ml). The organic phase was successively washed with 5% aqueous NaHCO$_3$ (75 ml) and saturated aqueous NaCl solution (3×75 ml), and then dried over Na$_2$SO$_4$ and filtered. Evaporation of the solvent under vacuum with external temperature of 35° C. led to 2.05 g of (RS,RS)-α-(2-ethoxy-phenoxy)-benzyl-oxirane with a chromatographic title of 97%, NMR (CDCl$_3$) 90 MHz δ : 1.4 (3H, t); 2.70 (2H, m); 3.25 (H, m); 4.03 (3H, q); 4.75 (H, d); 6.85 (4H, m); 7.30 (5H, bs).

EXAMPLE 6

To a solution of α-(2-ethoxy-phenoxy)-benzyl-oxirane (4.9 g) in methanol (50 ml), 32% aqueous ammonia (50 ml) was added. The reaction mixture was then stirred for 6 hours at room temperature in an hermetically sealed vessel. The reaction mixture was then concentrated under vacuum and the residue taken up with 99% ethanol (2×50 ml) and then with benzene (50 ml), each time evaporating the solvent to dryness. Crystallization of the residue with ethyl acetate led to 1-amino-2-hydroxy-3-(2-ethoxy-phenoxy)-3-phenyl-propane as single RS,RS diastereoisomer, m.p. 105°–107° C.

In analogous fashion, starting from suitable intermediates prepared according to the procedures described in the examples 1 to 5, the compound 1-amino-2-hydroxy-3-(4-trifluoromethyl-phenoxy)-3-phenyl-propane was obtained as single RS,RS diastereoisomer.

EXAMPLE 7

To a solution of (RS,SR) 1,2-dihydroxy-3-(2-ethoxy-phenoxy)-3-phenyl-propane (5 g) in pyridine (50 ml), cooled to −10° C., a solution of p-toluenesulfonyl chloride (3.9 g) in pyridine (50 ml) was added dropwise in 1.5 hours. The reaction mixture was stirred at −10° C. for 30 minutes then was left to reach the room temperature, stirred for further 3 hours and finally poured into a mixture of 2N aqueous HCl (1 l) and ice (650 g).

After extraction with ethyl acetate, the organic phase was successively washed with water (400 ml), 5% aqueous NaHCO$_3$ (400 ml) and saturated aqueous NaCl, dried over Na$_2$SO$_4$ and filtered.

Evaporation of the solvent under vacuum led to a residue which was purified on chromatographic column (toluene: acetone 190:7.5 as eluant) to give 4.3 g of (RS,SR)-1-(p-toluene-sulfonyloxy)-2-hydroxy-3-(2-ethoxy-phenoxy)-3-phenyl-propane, NMR (CDCl$_3$) 90 MHz, δ : 1.41 (3H, t); 2.42 (3H, s); 3.13 (1H, br); 4.04 (2H, q); 4.0–4.3 (3H, m); 5.01 (1H, d); 6.6–7.8 (13H, m).

EXAMPLE 8

To a solution of (RS,SR)-1-(p-toluenesulfonyloxy)-2-hydroxy-3-(2-ethoxy-phenoxy)-3-phenyl-propane (4.3 g) in dimethylacetamide (125 ml), 30% aqueous ammonia (125 ml) was added and the reaction mixture was kept for 12 hours at room temperature in an hermetically sealed vessel. The mixture was then concentrated under vacuum to a small volume, poured into water, saturated with NaCl, and extracted with ethylacetate.

The organic phase was washed with water, dried over Na₂SO₄, filtered, and the solvent evaporated under vacuum. The obtained oily residue was purified on chromatographic column (CHCl₃:CH₃OH:NH₄OH 180:20:2 as eluant), to give 1,1 g of 1-amino-2-hydroxy-3-(2-ethoxy-phenoxy)-3-phenyl-propane as single RS,SR diastereoisomer, m.p. 115°–117° C. In analogous fashion, using appropriate starting compounds prepared according to the procedure described in the example 1, 2 and 7, the compound 1-amino-2-hydroxy-3-(4-trifluoromethyl-phenoxy)-3-phenyl-propane was obtained as single RS,SR diastereoisomer, m.p. 120°–122° C.

We claim:

1. (RS,RS)- or (RS,SR)-1-amino-2-hydroxy-3-(2-ethoxy-phenoxy)-3-phenyl-propane.

* * * * *

UNITED STATES PATENT AND TRADEMARK OFFICE
CERTIFICATE OF CORRECTION

PATENT NO. : 5,068,433
DATED : November 26, 1991
INVENTOR(S) : MELLONI et al

It is certified that error appears in the above-identified patent and that said Letters Patent is hereby corrected as shown below:

On the cover page, item [75], the second inventor's name, please change "D." to --DELLA--.

Col. 3, line 27, please change "SR" to --RS--.

Signed and Sealed this

Thirty-first Day of August, 1993

*Attest:*

BRUCE LEHMAN

*Attesting Officer*     *Commissioner of Patents and Trademarks*